United States Patent [19]

Cree et al.

[11] 4,426,453
[45] Jan. 17, 1984

[54] DERIVATIVES OF IODOTHYRONINE COMPOUNDS AND THEIR USE IN AN ASSAY FOR THE FREE IODOTHYRONINE COMPOUNDS

[75] Inventors: Gavin M. Cree, Chalfont St. Giles; Terence A. Wilkins, Chesham; Reginald Monks, Great Missenden; David P. Nowotnik, Aylesbury, all of England

[73] Assignee: Amersham International Limited, England

[21] Appl. No.: 297,086

[22] Filed: Aug. 27, 1981

[30] Foreign Application Priority Data

Sep. 18, 1980 [GB] United Kingdom ............... 8030260
Feb. 6, 1981 [GB] United Kingdom ............... 8103673

[51] Int. Cl.$^3$ ................... G01N 33/58; G01N 33/60
[52] U.S. Cl. .................................. 436/500; 436/542; 436/543; 436/544; 436/545; 436/804
[58] Field of Search ............ 424/1; 436/500, 542–545

[56] References Cited

U.S. PATENT DOCUMENTS 4,332,784  6/1982  Smith et al. ........................... 424/1
4,352,751  10/1982  Wieder et al. ..................... 424/1 X

OTHER PUBLICATIONS

Kjeld et al., Clinica Chimica Acta, 61 (1975) 381–389.
Radioassay Systems in Clinical Endocienology, Ed. Abraham, Marcel Dekrer, Inc., N.Y., 1979, 101–115.

Primary Examiner—Christine M. Nucker
Attorney, Agent, or Firm—Wenderoth, Lind & Ponack

[57] ABSTRACT

Novel amides of an iodothyronine compound such as tri-iodothyronine (T3) or thyroxine (T4) with an aminoacetic acid compound such as nitrilotriacetic acid (NTA), ethylenediaminetetraacetic acid (EDTA) or diethylenetriamine pentaacetic acid (DTPA) may be labelled, e.g. radioactively labelled with I-125, to give labelled derivatives useful in assays of a free thyroid hormone in a biological fluid which also contains the thyroid hormone bound to one or more natural binders. The novel compound T4 EDTA is shown to bind much more strongly to antibodies to T4 than to the natural protein binders in the biological fluid.

9 Claims, No Drawings

DERIVATIVES OF IODOTHYRONINE COMPOUNDS AND THEIR USE IN AN ASSAY FOR THE FREE IODOTHYRONINE COMPOUNDS

This invention relates to derivatives of iodothyronine compounds and their use in an assay for the free iodothyronine compounds. The novel derivatives are those having the general formula.

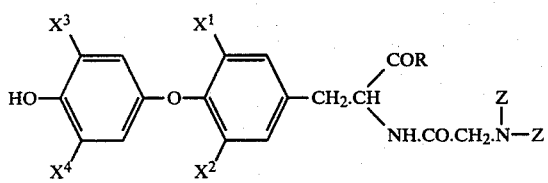

where each of $X^1$, $X^2$, $X^3$, and $X^4$ is independently Cl, Br, I or H, with the provisos that at least one of $X^1$, $X^2$, $X^3$, and $X^4$ is I, and that at least two of $X^1$, $X^2$, $X^3$, and $X^4$ are halogen, R is OH, amino, alkylamino, dialkylamino, or alkoxyl, each Z is independently $-(CH_2)_nNZ_2$ or $-CH_2COR$, and n is 1, 2 or 3.

The nature of each group R is independent of the others. Preferably all groups R are hydroxyl.

Preferably Z is $-(CH_2)_nNZ_2$ at nought, one or two places in the molecule, and is $-CH_2COR$ at the remaining places.

The compounds are amides of an iodothyronine compound and an amino acetic acid compound.

| Iodothyronine compounds envisaged include | | | | | |
|---|---|---|---|---|---|
| Compound | Abbreviation | $X^1$ | $X^2$ | $X^3$ | $X^4$ |
| Di-iodothyronine | | I | H | I | H |
| Tri-iodothyronine | T3 | I | H | I | I |
| Reverse tri-iodothyronine | r-T3 | I | I | I | H |
| Thyroxine | T4 | I | I | I | I |
| 3'-Bromo-5'-iodo-3,5-di-iodothyronine | | I | I | I | Br |
| 3'-Chloro-5'-iodo-3,5-di-iodothyronine | | I | I | I | Cl |

| Aminoacetic acid compounds envisaged include | | | |
|---|---|---|---|
| Compound | Abbreviation | Number of places in molecule where Z is $-(CH_2)_nNZ_2$ | Value of n in each group Z |
| Nitrilotriacetic acid | NTA | 0 | — |
| Ethylenediamine tetraacetic acid | EDTA | 1 | 2 |
| Diethylenetriamine pentaacetic acid | DTPA | 2 | 2 |

Of particular interest and importance is the amide of thyroxine and EDTA, hereinafter called T4.EDTA.

These compounds have an asymmetric carbon atom and are accordingly optically active. The invention envisages the L-isomers, the D-isomers and mixtures of the two. Naturally occurring iodothyronine compounds are L-isomers. For use in the method described below, D-isomers of compounds according to the invention may have particularly advantageous properties.

Our European Patent Specification No. 0026103 describes and claims a method of determining the concentration of a free thyroid hormone in a biological fluid which also contains the thyroid hormone bound to one or more natural binders, by:

(a) admixing a sample of the fluid with a labelled derivative of the thyroid hormone, and with a specific binder for the thyroid hormone.

(b) effecting reaction between the free thyroid hormone, the labelled derivative thereof and the specific binder, (c) if necessary, separating that portion of the thyroid hormone and labelled derivative thereof that has become bound to the specific binder from that portion not so bound, (d) measuring the amount of the labelled derivative of the thyroid hormone that is, or is not, bound to the specific binder, and (e) using the said measurement to determine the concentration of free thyroid hormone in the biological fluid, wherein the labelled derivative of the thyroid hormone is chosen to bind strongly to the added specific binder, but to bind not at all, or much more weakly than does the thyroid hormone, to the natural binders in the biological fluid.

The thyroid hormone is selected from thyroxine and tri-iodothyronine.

The specific binder will generally be an antibody to the thyroid hormone, or possibly a naturally occurring protein binder isolated from suitable biological materials.

The labelled derivative of the thyroid hormone has been chemically modified to inhibit its binding to the natural thyroid hormone binders, while retaining its ability to bind to the specific assay binder. At the same time, this derivative also contains or has linked to it a physical marker, such as a radioactive atom (or atoms) a fluorophor, a light chromophore, an enzyme or a chemi-luminescent group. When radioactive labelling is used, Iodine-125 is a suitable isotope, but others will readily occur to those skilled in the art. It is essential that this labelled derivative of the thyroid hormone binds much less strongly (or not at all) to the natural thyroid hormone binders of the biological sample than to the added specific assay binder, though binding of the labelled derivative of the thyroid hormone to minor weakly binding components of the natural thyroid hormone binders in the biological sample does not necessarily invalidate the method.

Because the labelled derivative does not significantly bind to the natural binding proteins, it is substantially all available for competition with the free thyroid hormone for reaction with the specific binder. It is in consequence possible to use a low concentration of specific binder while still obtaining a satisfactory dose-responsive curve. The use of a low concentration of specific binder is advantageous in that it does not lead to significant removal of thyroid hormone from the natural protein binders in the system.

Thyroxine (T4) is transported in the blood stream of human beings largely bound to the three naturally occurring T4-binding proteins TBG, TBPA and Albumin. The percentage of T4 bound to each of these is approximately 70%, 20-25% and 5-10% respectively. In synthesising a tracer for this particular assay it is important that the binding of the tracer to TBG and TBPA in the assay is zero or very much less than the binding of T4 to these two proteins. In this particular assay the binding requirements for the tracer with serum albumin are less stringent because only a small percentage of T4 is bound to albumin and the number of empty albumin binding sites is very large compared to the number of sites with T4 bound to them. This means that substantial quantities of tracer can be bound to serum albumin without displacement of any T4 that is bound.

A number of possible modifications of the thyroxine molecule are discussed in the said European Patent Specification No. 7,933,072, but the compound tested in the Examples is N-acetyl-thyroxine-methyl ester labelled with I-125. It has now been discovered, and this forms the basis of the present invention, that T4.EDTA, when labelled with I-125, has properties which are surprisingly and substantially superior to those of N-acetyl-thyroxine-methyl ester, for use in the said test. Specifically:

1. N-Acetyl-thyroxine-methyl ester only gives useful assay results within hours of dilution into the assay buffer. It is suspected to be hydrolysing on contact with water, and cannot therefore be supplied as a liquid reagent in a kit. On the other hand, T4.EDTA is stable in water.

2. N-Acetyl-thyroxine-methyl ester binds significantly to polystyrene assay tubes, which gives rise to higher blank results than are desired. On the other hand, T4.EDTA shows no significant tendency to bind to assay tubes.

3. N-Acetyl-thyroxine-methyl ester binds appreciably to TBG and, it is suspected, also to albumin. On the other hand, T4.EDTA shows no significant tendency to bind to TBG (see Example 2 below).

4. When serum samples are diluted with water or buffer and then assayed in a total-T4 assay, the measured total-T4 values decrease in proportion to the dilution of the sample.

It has been shown theoretically (J. H. H. Oppenheimer and M. I. Surks, J. Clin. Endocrinology and Metabolism, 24, p.785-793 (1964) that the free-T4 concentration of human serum samples is unaffected by dilution within certain limits.

When this is tested using the assay of our European Patent Specification No. 7,933,072, it is found to be only approximately true for N-acetyl-thyroxine-methyl ester but much more accurately true for T4.EDTA.

This invention accordingly includes use of the compounds of the present invention, after labelling, in the method of our European Patent Specification No. 0026103.

The compounds of the present invention are readily prepared by known methods. The amino acetic acid compound may be converted to an anhydride which is then reacted with the amino group of the iodothyronine compound. The product may be precipitated in acid solution, and purified by chromatography. Esters and amides may be made using standard chemical reactions.

The following Examples illustrate the invention.

EXAMPLE 1

Preparation of 1,2-bis(2,6-dioxo-4-morpholinyl)ethane

To a 250 ml round bottomed flask fitted with a magnetic stirrer, condenser, and a drying tube (calcium chloride), was added pyridine (dried by distillation from potassium hydroxide) (80 ml). Ethylenediaminetetraacetic acid (29.12 g) was added followed by acetic anhydride (37.6 ml). The suspension was stirred and heated at 65°-80° C. for 7 hr. The mixture was cooled overnight and the white solid filtered off. The solid was washed once with pyridine (dry 20 ml) and four times with ether (dry 4×40 ml). The white solid was dried on a manifold and stored in a desiccator.

Yield 18 g, M.pt. 193°-7° decomp.

Preparation of 1-{3',5'-di-iodo-4'(3'',5''-di-iodo-4''-Hydroxyphenoxy)-phenyl}2-carboxy-6,9-dicarboxymethyl-4-oxo-3,6,9-triazaundecan-11-oic acid (T4.EDTA)

Thyroxine, sodium salt pentahydrate (1.5 g) was suspended in dry pyridine (10 ml) and stirred vigorously.

A three necked flask was fitted with a stopper, a thermometer and a condenser with a drying tube (calcium chloride) attached. Dry pyridine (100 ml) was added and the solvent was stirred vigorously and heated to 95° C.

1,2-bis(2,6-dioxo-4-morpholinyl)ethane (2.0 g) was dissolved in the hot solvent. Whilst stirring, the suspension of thyroxine, sodium salt pentahydrate, was added to the hot solution in approximately eight equal portions over a period of five minutes using a wide bore tube. The solution was maintained at 95° C. for a further three minutes and was then allowed to cool to room temperature.

Water (15 ml) was added and ethylenediaminetetraacetic acid started to precipitate. The mixture was left overnight, filtered, and the residue washed with pyridine. The filtrate and washings were combined and pumped to dryness on a rotary evaporator, then pumped on a manifold to remove final traces of pyridine. The resulting solid was redissolved in ammonia (1 M, 35 ml) and the solution was centrifuged to remove any insoluble material. The clear yellow solution was adjusted to pH 1 with concentrated hydrochloric acid (~15 ml) to reprecipitate the solid. The white precipitate was filtered and washed with water until the filtrate had a pH>4. The solid was freeze dried.

Chromatographic Purification of T4.EDTA

The crude product, 1.5853 mg was dissolved in 5½ ml of 2MNH3(aq), approximately 300 mg per ml. On initial addition of 2MNH3(aq) the white solid started turning black, but on further addition of the 2MNH3(aq) only a yellow/brown tinted clear solution was present.

The crude product was applied to 32 Merck silica, 5717, preparative plates, giving a loading of 50 mg of crude product per plate. The plates were run in n-butanol/water/acetic acid (60/25/15). When the plates had run to within ½ an inch of the top, they were removed from the tanks and put in a stream of air at room temperature, to dry.

Under ultra-violet light 4 or 5 bands were visible, one on the base line, one at rf 0.75 which was T4 and a group of 2 or 3 bands in between, it being hard to distinguish between the top two of this group. The desired band, the slowest of the middle group was removed.

The silica that was removed was washed with 0.2MNH3(aq), (10 ml of 0.2MNH3(aq) per plate). This gave a total of 320 ml of 0.2MNH3(aq) needed for washing, giving a yellow tinted clear solution. The solution was then acidified using concentrated HCl to pH 2, thus giving rise to a white precipitate and a decolourising of the solution. The precipitate was obtained by centrifugation and washed with 20 ml of water three times, or until the pH of the supernatant was approximately 7. The white solid was then freeze dried on the vacuum manifold. Yield of dry product was 855 mg.

The product from above was dissolved in 3 ml of 2MNH₃(aq) and applied to 16 cellulose (Anachem, Avicell F, 1000 μm thick) preparative plates. The plates were run in n-butanol/water/acetic acid (60/25/15). These plates run appreciably faster than the silica preparative plates. When the plates had run they were dried in a stream of air at room temperature. Under ultra-violet light only one band was seen, but a yellow band visible to the naked eye was present just above the band that was visible under ultra-violet light. The band visible under ultra-violet light was removed and the cellulose washed with 10 ml of 0.2MNH₃(aq) for every plate, totalling 160 ml of 0.2MNH₃(aq). The yellow tinted solution collected was then acidified using concentrated HCl to pH 2, giving rise to a white precipitate and decolourising the solution. The precipitate was centrifuged down and the supernatant was discarded, the precipitates were combined and washed using 20 ml of water per tube. The combined precipitate was washed until the pH of the supernatant was approximately 7. The white solid remaining was then freeze-dried. This material gave a single spot on silica TLC when run in n-butanol/water/acetic acid (60/25/15). Yield 89.2 mg.

|  | % Expected | Results % | | | Mean |
|---|---|---|---|---|---|
| Carbon | 28.56 | 27.97 | 27.97 | 27.84 | 27.93 |
| Hydrogen | 2.40 | 2.47 | 2.57 | 2.34 | 2.46 |
| Nitrogen | 4.00 | 3.74 | 3.68 | 3.74 | 3.72 |

Spectroscopic data confirmed the structure of the compound. The UV spectrum was similar to that of thyroxine. The IR spectrum was characterized thus:

| Wave No (cm$^{-1}$) | Intensity | Assignment |
|---|---|---|
| 3550-2550 | M(Broad) | O—H |
| 2920 and 2850 | W | C—H |
| 1720 | M-S | C=O |
| 1625 | S | C=O |
| 1585 | Shoulder | Aromatic C=C |
| 1550 | Shoulder | N—H and C—N comb. |
| 1505 | W | Aromatic C=C |
| 1455 | M | Aromatic C=C |
| 1440 | S | CH₂ |
| 1395 | S | C—O and OH comb. |
| 1320 | W | C—N |
| 1235 | M-S |  |
| 1050 | W | Phenol |

EXAMPLE 2

Preparation of
1,5bis(2,6-dioxo-4-morpholinyl-3-aza-3-carboxymethyl-pentane

A suspension of diethylene triamine pentacetic acid (6.35 g) in acetic anhydride (9.5 ml) and pyridine (8.4 ml), in a flask fitted with a drying tube (calcium chloride), was maintained at room temperature for 5 days with occasional stirring. The yellow product was filtered off, washed with diethyl ether (50 ml) and dried.

The product was identified as the title compound by IR spectroscopy.

MP 175°–180° C., Yield 4.56 g.

Preparation and purification of
2-carboxy-6,9,12-tricarboxymethyl
1-{3'5'-diiodo-4'[(3"5"-diiodo-4"-hydroxy)phenoxy]-phenyl}-4-oxo3,6,9,12 tetraazatetradecane-14-oic acid
(T4.DTPA)

Thyroxine, sodium salt (100 mg) was suspended in pyridine (50 ml), stirred and warmed to 90°. Most of the solid dissolved The bis anhydride derived from DTPA (486 mg) was added, dissolving rapidly, and the mixture maintained at 90° for 10 minutes. The mixture was then allowed to cool to room temperature. After 2½ hours, 2 ml of water was added, and the mixture allowed to stand overnight. A small precipitate was filtered off and discarded. The solvent was evaporated to give a yellow/white solid.

The purification was carried out in a manner analogous to that for T4.EDTA with a corresponding reduction in the number of tlc plates used Yield 6.3 mg.

The product had an Rf of 0.19 on silica gel plates run in butan-1-ol/water/acetic acid (60/25/15).

The compound was identified from its IR and UV spectra.

EXAMPLE 3

Preparation of 2-carboxy-6,9-dicarboxymethyl-1 3',5'di-iodo-4'(3"-iodo-4"-hydroxy)phenoxy phenyl 4-oxo-3,6,9-triazaundecan-11-oic acid. (T3.EDTA)

This preparation was carried out in the same manner as that of T4.EDTA, employing 2.006 g of EDTA bis anhydride (see example 1) and 1.496 g of T3, as its sodium salt.

The chromatographic purification was also carried out as described in Example 1, using 700 mg of the crude product, about half of the yield obtained, and using proportionately reduced numbers of silica gel and cellulose tlc plates.

Yield 32.5 mg.

The compound was identified by IR and UV spectroscopy, giving spectra scarcely distinguishable from those of T4.EDTA, as cited previously. The nature of the compound was confirmed by its binding to Antisera (having low T4 cross reactivity) where the compound had equal, or better, binding than T3 itself.

EXAMPLE 4

Method for estimation of T4.EDTA binding strength to TBG and prealbumin relative to that of T4

1. Principle of the method

Pre-precipitated antiserum (binding reagent) to either TBG or prealbumin is incubated with a serum source of TBG or prealbumin, so that the T4 binding protein is isolated on the binding reagent. Tracer $^{125}$I-T4 is added to the resulting complex and is thus purified. The displacement of the tracer $^{125}$I-T4, by varying concentrations of T4 and T4.EDTA, from the TBG or prealbumin, can then be studied. The results can be used to estimate the differences in binding affinity between T4 and T4.EDTA for the two T4 binding proteins.

2. Method

2.1 Preparation of $^{125}$I-T4:TBG:anti-TBG binding reagent

2.1.1 Binding reagent preparation

| 15% Donkey anti-sheep | in phosphate |
|---|---|
| 2% TBG Antiserum | buffer + 0.05% BSA |

Equal quantities of the above solutions are mixed and rotated overnight at 4° so that the final concentrations in the binding reagent are 7.5% donkey anti-sheep, and 1% TBG antiserum. Centrifugation at 900 rpm, decantation and resuspension in fresh buffer are carried out twice to wash the reagent.

2.1.2 Formation of TBG:anti-TBG binding reagent 1 ml of resin stripped human serum and 20 ml of the above binding reagents are mixed for 1 hour at room temperature. Centrifugation, decantation and resuspension in fresh buffer (phosphate+0.05% BSA) are carried out twice.

2.1.3 Formation of $^{125}$I-T4:TBG:anti-TBG binding reagent

Typically 10 ml of TBG:anti-TBG binding reagents, 28 ml of phosphate buffer+0.05% BSA, and 2 ml of $^{125}$I-T4 tracer solution (0.1 μCi high specific activity T4 per ml in phosphate buffer+0.05% BSA) are mixed for 1 hour at room temperature. Centrifugation, decantation and resuspension in fresh buffer (phosphate+0.05% BSA) are carried out twice. Once prepared the tracer T4:TBG:anti-TBG binding reagent is used immediately.

2.1.4 T4 and T4.EDTA concentrations

The stock solutions are diluted in phosphate buffer+0.005% BSA. The range of T4 concentrations used is ≃2000–2 ng/ml (≃100–0.1 pMol/tube). The range of T4.EDTA concentrations used is ≃8000–8 ng/ml (≃400–0.4 pMol/tube).

2.2 Preparation of $^{125}$I-T4:TBPA:anti-TBPA binding reagent

2.2.1 Binding reagent preparation

This is prepared as for the anti-TBG binding reagent except that equal volumes of 30% donkey anti-rabbit second antibody and 4% TBPA antiserum solutions were mixed to give final concentrations of 15% donkey anti-rabbit, and 2% anti-TBPA.

2.2.2 Formation of TBPA:anti-TBPA binding reagent

600 μl normal serum and 20 ml anti-TBPA binding reagent are mixed for 1 hour at room temperature. The washing of the reagent is as for TBG, except that the buffer used is phosphate+0.005% BSA.

2.2.3 Formation of $^{125}$I-T4:TBPA:anti-TBPA binding reagent

Typically 20 ml of the above TBPA:anti-TBPA binding reagent, 16 ml phosphate buffer+0.005% BSA, and 4 ml $^{125}$I-T4 tracer solution (high specific activity T4, 0.2 μCi/ml in phosphate+0.005% BSA) were mixed at room temperature for 1 hour. Washing of the complex is as for the tracer-TBG complex, except that phosphate buffer+0.005% BSA is used. Once formed, the $^{125}$I-T4:TBPA:anti-TBPA binding reagent complex is used immediately.

2.2.4 T4 and T4.EDTA concentrations

The stock solution is diluted in phosphate buffer+0.005% BSA. The range of T4 concentrations used is ≃8000–8 ng/ml (≃400–0.4 pMol/tube). The range of T4.EDTA concentrations used is ≃8000–8 ng/ml (≃400–0.4 pMol/tube).

2.3 Assay procedure for both TBG and prealbumin

50 μl of T4 or T4.EDTA dilution
1000 μl of tracer:binding reagent complex
Vortex
1 hour at 37° C.
Vortex
1 hour at 37° C.
Vortex
Centrifuge at >1500 rpm, decant., count.

Thus the percentage bound of the tracer at different T4 and T4.EDTA concentrations, can be determined in the two systems.

3. Calculation of results

Tracer percentage bound is plotted against T4 and T4.EDTA concentrations, and from these curves an estimate of the non-specific binding can be made. The data can then be re-calculated, using this blank correction, plotted, and the T4 and T4.EDTA concentrations corresponding to a range of tracer percentage bound values can be read off the curve. The ratio between the concentrations of T4 and T4.EDTA that give the same displacement of tracer is described by the equation:

$$\frac{X_{T4.EDTA}}{X_{T4}} = \frac{K_A T4.EDTA}{K_A T4} + y\left(1 - \frac{K_A T4.EDTA}{K_A T4}\right)$$

where
y = fraction of tracer T4 bound
$X_{T4.EDTA}$ = concentration of T4.EDTA at y
$X_{T4}$ = concentration of T4 at y
$K_A T4$ = affinity constant of T4 for particular binder
$K_A T4.EDTA$ = affinity constant of T4.EDTA for particular binder Hence plotting the ratio against y, the fraction of tracer T4 bound, both the intercept and slope may be used to estimate the ratio of the affinity constants.

By this technique it was estimated that T4.EDTA bound to TBG with only 3.5% of the affinity constant of T4, and to TBPA with only 2.7% of the affinity constant of T4.

It has also been determined that the affinity constant of T4.EDTA with respect to T4 antiserum is 90.4% of that of T4.

Thus T4.EDTA binds only very weakly to TBG and TBPA, the two main binding proteins which occur naturally in serum; but binds almost as strongly to T4 antiserum as does T4 itself.

EXAMPLE 5

Free-T4 assay using T4.EDTA tracer

1. Tracer $^{125}$I-T4. EDTA

T4.EDTA was labelled with $^{125}$I by an exchange reaction using sodium iodide-$^{125}$I and chloramine-T. The specific activity obtained was typically 500 millicuries per milligram, and was used as a working concentration of 0.13 microcuries per millimeter in a 60 millimolar phosphate buffer, pH 7.4, containing 0.9% sodium chloride, 0.9% bovine serum albumin and 0.1% sodium azide.

2. Solid phase T4 antibody suspension

A solid phase antibody was used consisting of T4-specific antiserum bound on to micron sized latex particles such that the suspension contained 0.66 milligram of latex particles per milliliter and antibodies from 0.5 microliters of T4-specific antiserum per milligram of latex. The buffer was 10 millimolar phosphate, pH 7.4 containing 0.1% sodium azide.

3. Free-T4 serum standards

A set of 6 human serum pools were prepared by standard techniques to contain free-T4 concentrations ranging from zero to approximately 10 nanograms per deciliter. These standards were calibrated with reference to an equilibrium dialysis free T4 assay.

4. Assay method

The free T4 assay was set up in polystyrene assay tubes following this protocol:
100 µl serum standard or unknown serum sample
500 µl $^{125}$I-T4.EDTA tracer solution.
500 µl solid phase T4 antibody suspension.

The assay tubes were vortex mixed, and incubated at 37° C. in a water bath for one hour. The tubes were centrifuged at 1500 g for 20 minutes and the supernatant liquid decanted. The readioactivity of the precipitate was measured.

5. Standard curve results

The following results were typical of those obtained by this technique:

| free T4 ng/dl | % radioactivity in solid phase |
|---|---|
| 0 | 61.8 |
| 0.45 | 41.2 |
| 0.95 | 30.8 |
| 1.9 | 21.1 |
| 4.9 | 12.4 |
| 9.0 | 9.3 |

EXAMPLE 6

Correlation of Free-T4 RIA method using T4.EDTA with the equilibrium dialysis method of Free T4 determination 73 serum samples of various thyroid status were measured in the free T4 assay described herein and also in an equilibrium dialysis free T4 assay. The equilibrium dialysis method employed an overnight dialysis of the serum samples at 37° C. followed by a sensitive T4 RIA of the dialysate. (This method was based on that described by Ellis S. M. and Ekins R. P., 1975, "The radioimmunoassay in Clinical Biochemistry" (Ed. Pasternak), 187-194, Heyden, London).

Linear regression analysis of the data showed a good correlation, r=0.98 between the two sets of results.

EXAMPLE 7

Normal range determination and discrimination from hypo- and hyperthyroid cases

Measurement of serum samples from approximately 520 euthyroid patients in the free T4 assay described herein enabled the non-parametic normal range to be estimated as 0.7-1.8 ng/dl.

The level of discrimination from 41 hypothyroid cases and 35 hyperthyroid cases was superior to that obtained by measuring free thyroxine index (F.T.I.) on the same samples. Specifically, 6 out of 41 hypothyroid cases and 3 out of 35 hyperthyroid cases were mis-diagnosed by the FTI technique; however, 4 out of 41 hypothyroid cases and 0 out of 35 hyperthyroid cases were mis-diagnosed by the free-T4 assay of the present invention.

Results of high and low TBG euthyroid cases

The table below shows that euthyroid non-pregnant cases with abnormally high or low TBG levels have total T4 levels that are significantly higher or lower than normal. A total T4 result alone here would be misleading in the thyroid diagnosis, and even remains misleading when combined with a T3-Uptake result to give an F.T.I. value. The free T4 level obtained by the assay described herein, however, remains normal and gives the correct diagnosis.

Table of high and low TBG euthyroid cases

| | Patient No. | free-T4 ng/dl | Total T4 µg/dl | TBG µg/ml | T3 Uptake | F.T.I. n moles/ liter |
|---|---|---|---|---|---|---|
| High TBG cases | 875 | 1.58 | 20.9 | 50.2 | 19.9 | 53.5 |
| | 1010 | 1.63 | 18.9 | 47.4 | 21.8 | 53.0 |
| | 1134 | 1.8 | 22.5 | 63.4 | 18.5 | 53.6 |
| Low TBG cases | 1110 | 1.5 | 1.7 | 0.3 | 44.4 | 9.7 |
| | 973 | 0.88 | 2.3 | 6.0 | 43.3 | 13.0 |
| | 985 | 1.25 | 2.5 | 3.8 | 45.9 | 14.7 |
| | 978 | 1.9 | 2.2 | 1.1 | 47.6 | 13.3 |
| | 979 | 0.9 | 3.9 | 1.1 | 43.1 | 21.6 |
| | 983 | 1.21 | 2.0 | 2.3 | 47.2 | 12.3 |
| | 984 | 1.26 | 2.6 | 5.6 | 42.4 | 14.4 |
| | 980 | 1.5 | 2.0 | 0.2 | 47.8 | 12.4 |
| | 981 | 1.3 | 2.6 | 1.7 | 47.3 | 16.1 |
| Normal ranges | | 0.7-1.8 | 5.3-12.4 | 9.6-26.9 | 25.5-34.4 | 23-48 |

F.T.I. is calculated as described in Clark F and Horn D. B., J. Clin. Endocrin. and Metab., 25, 1965, 39-45. The formula is F.T.I.=(Total T4 (µg/dl)×T3 Uptake×12.87÷100.

We claim:
1. A derivative of an iodothyronine compound having the general formula

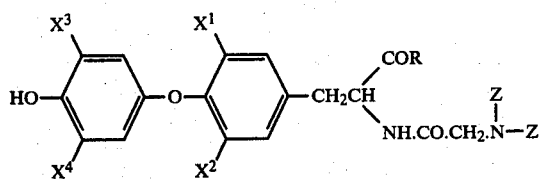

where
each of $X^1$, $X^2$, $X^3$, and $X^4$ is independently Cl, Br, I or H, with the provisos that at least one of $X^1$, $X^2$, $X^3$ and $X^4$ is I, and that at least two of $X^1$, $X^2$, $X^3$ and $X^4$ are halogen, R is OH, amino, alkylamino, dialkylamino or alkoxyl, each Z is independently —$(CH_2)_n$ $NZ_2$ or —$CH_2COR$, and n is 1, 2 or 3, said derivative being radioactively labelled with iodine-125.

2. The derivative as claimed in claim 1, wherein Z is —$(CH_2)_n NZ_2$ at nought, one or two places in the molecule and is —$CH_2COR$ at the remaining places.

3. The derivative as claimed in claim 1, which is an amide of an iodothyronine compound selected from di-iodothyronine, tri-iodothyronine, reverse tri-iodothyronine, thyroxine, 3'-bromo-5'-iodo-3,5-di-iodothyronine and 3'-chloro-5'-iodo-3,5-di-iodothyronine.

4. The derivative as claimed in claim 1, which is an amide of an aminoacetic acid compound selected from nitrilotriacetic acid, ethylenediamine tetraacetic acid and diethylenetriamine pentaacetic acid.

5. The derivative as claimed in claim 1, which is an amide of tri-iodothyronine or thyroxine with ethylenediamine tetraacetic acid or diethylenetriamine pentaacetic acid.

6. The derivative as claimed in claim 1, which is the amide of thyroxine with ethylenediamine tetraacetic acid.

7. A method of determining the concentration of a free thyroid hormone in a biological fluid which also contains the thyroid hormone bound to one or more natural binders, by:

(a) admixing a sample of the fluid with a labelled derivative of the thyroid hormone, and with a specific binder for the thyroid hormone, (b) effecting reaction between the free thyroid hormone, the labelled derivatives thereof and the specific binder, (c) if necessary, separating the portion of the thyroid hormone and labelled derivative thereof that has become bound to the specific binder from that portion not so bound, (d) measuring the amount of the labelled derivative of the thyroid hormone that is, or is not, bound to the specific binder, and (3) using the said measurement to determine the concentration of free thyroid hormone in the biological fluid, wherein the labelled derivative of the thyroid hormone is chosen to bind strongly to the added specific binder, but to bind not at all, or much more weakly than does the thyroid hormone, to the natural binders in the biological fluid, and is selected from the derivative of an iodothyronine compound having the general formula

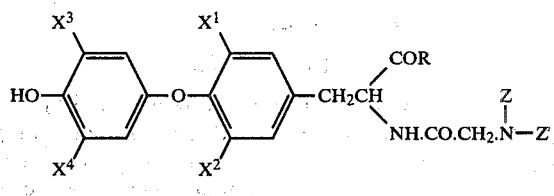

where
each of $X^1$, $X^2$, $X^3$, and $X^4$ is independently Cl, Br, I or H, with the provisos that at least one of $X^1$, $X^2$, $X^3$ and $X^4$ is I, and that at least two of $X^1$, $X^2$, $X^3$ and $X^4$ are halogen, R is OH, amino, alkylamino, dialkylamino or alkoxyl,
each Z is independently —$(CH_2)_n$ $NZ_2$ or —$CH_2COR$, and n is 1, 2 or 3, said derivative being radioactively labelled with iodine-125.

8. The method as claimed in claim 7, wherein the thyroid hormone is tri-iodothyronine or thyroxine and the derivative is an amide of tri-iodothyronine or thyroxine with ethylenediamine tetraacetic acid or diethylenetriamine pentaacetic acid.

9. The method as claimed in claim 7, wherein the specific binder is used in a concentration so low as not to lead to significant removal of thyroid hormone from the natural protein binders.

* * * * *